United States Patent
Jacquin et al.

(10) Patent No.: US 10,508,062 B2
(45) Date of Patent: Dec. 17, 2019

(54) CONVERSION OF BUTANEDIOL INTO BUTADIENE, WITH SCRUBBING USING DIESTERS

(71) Applicants: IFP ENERGIES NOUVELLES, Rueil-Malmaison (FR); COMPAGNIE GENERALE DES ETABLISSEMENTS MICHELIN, Clermont-Ferrand (FR)

(72) Inventors: Marc Jacquin, Lyons (FR); Nuno Pacheco, Clermont-Ferrand (FR); Claire Fauvarque-Nuytten, Clermont-Ferrand (FR)

(73) Assignees: IFP ENERGIES NOUVELLES, Rueil-Malmaison (FR); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 16/302,320

(22) PCT Filed: May 9, 2017

(86) PCT No.: PCT/EP2017/061092
§ 371 (c)(1),
(2) Date: Nov. 16, 2018

(87) PCT Pub. No.: WO2017/198503
PCT Pub. Date: Nov. 23, 2017

(65) Prior Publication Data
US 2019/0161419 A1 May 30, 2019

(30) Foreign Application Priority Data
May 17, 2016 (FR) ..................................... 16 54375

(51) Int. Cl.
*C07C 1/213* (2006.01)
*C07C 7/06* (2006.01)
(Continued)

(52) U.S. Cl.
CPC ................ *C07C 1/213* (2013.01); *C07C 7/06* (2013.01); *C07C 7/11* (2013.01); *C07C 67/08* (2013.01);
(Continued)

(58) Field of Classification Search
None
See application file for complete search history.

(56) References Cited

U.S. PATENT DOCUMENTS 2,345,113 A   3/1944   Guggemos
2,372,221 A   3/1945   Morell
(Continued)

OTHER PUBLICATIONS

International Search Report PCT/EP2017/061092 dated Jul. 17, 2017 (pp. 1-2).

*Primary Examiner* — Tam M Nguyen
(74) *Attorney, Agent, or Firm* — Millen White Zelano and Branigan, PC; John Sopp

(57) ABSTRACT

The invention pertains to a method for converting butanediol into butadiene that is fed with a butanediol feedstock, where said method comprises at least an esterification step, a pyrolysis step, and a step for separation of the pyrolysis effluent comprising at least one section for cooling said pyrolysis effluent and producing a liquid pyrolysis effluent and a steam pyrolysis effluent and a gas-liquid washing section that is fed at the top with a fraction of the butanediol diester effluent obtained from the esterification step and at the bottom with the steam pyrolysis effluent, where said section produces a butadiene effluent at the top and a washing effluent at the bottom.

16 Claims, 1 Drawing Sheet

(51) Int. Cl.
*C07C 7/11* (2006.01)
*C07C 67/08* (2006.01)
C07C 11/167 (2006.01)
C07C 69/16 (2006.01)

(52) U.S. Cl.
CPC ............ *C07C 11/167* (2013.01); *C07C 69/16* (2013.01); *Y02P 20/127* (2015.11)

(56) References Cited

U.S. PATENT DOCUMENTS

| | | | |
|---|---|---|---|
| 2,383,205 A | 8/1945 | Mattox | |
| 3,647,903 A * | 3/1972 | Maurin | C07C 1/24 585/327 |
| 2018/0022682 A1 * | 1/2018 | Richard | C07C 67/08 560/191 |
| 2018/0037519 A1 * | 2/2018 | Richard | C07C 67/08 |
| 2018/0370869 A1 * | 12/2018 | Pacheco | C07C 67/08 |

* cited by examiner

CONVERSION OF BUTANEDIOL INTO BUTADIENE, WITH SCRUBBING USING DIESTERS

TECHNICAL FIELD OF THE INVENTION

The invention relates to the production of 1,3-butadiene from butanediol.

PRIOR ART

Today, 95% of the production of 1,3-butadiene is provided by the steam-cracking of hydrocarbons and the subsequent extraction of the diolefins within a $C_4$ distillation fraction by extractive distillation methods.

The variation in the costs of the raw materials has caused the steam-cracking units to be operated with lighter and lighter and consequently less expensive feedstocks, leading to a reduction in the production of the $C_4$ fraction and consequently of 1,3-butadiene. Alternative methods for producing 1,3-butadiene should thus been found.

One method for producing 1,3-butadiene from 2,3-butanediol, implemented on a pilot scale in 1945 in the USA, is described in the patents FR 859902, U.S. Pat. Nos. 2,383,205, 2,372,221, and in *Industrial & Engineering Chemistry*, 37 (9), 1945, pp. 865 to 908. This method consists of two primary steps:

The esterification of 2,3-butanediol by a carboxylic acid to form the corresponding diester;

The pyrolysis of the diester to produce 1,3-butadiene and carboxylic acid, where the latter is recycled to the esterification step.

This method was developed because the direct dehydration of 2,3-butanediol leads to the very large majority formation of methyl ethyl ketone (MEK), and MEK cannot be dehydrated to form 1,3-butadiene. This method is particularly advantageous because the step for pyrolysis of the diester of 2,3-butanediol can be carried out with very good yields (typically more than 80 mol %), and the 1,3-butadiene that is obtained is of high purity (typically about 99% by weight).

Since the pyrolysis step simultaneously produces 1,3-butadiene and carboxylic acid, the butadiene-rich gas necessarily contains carboxylic acid, which has to be eliminated. A classic solution consists of washing with water. However, this washing produces a gas that is rich in hydrated 1,3-butadiene, which cannot be directly treated by cryogenic distillation or extractive distillation at high pressure since gas hydrates may be formed. Preliminary drying of the hydrated butadiene-rich gas is thus required.

This invention makes it possible to simplify the system for treating the butadiene-rich gas. In point of fact, the applicant has discovered that the carboxylic acid contained in the butadiene-rich gas could be efficiently eliminated by carrying out a gas-liquid washing operation with the diester intermediate product.

OBJECT AND ADVANTAGE OF THE INVENTION

The invention pertains to a method for converting butanediol into butadiene that is fed with a butanediol feedstock, where said method comprises at least:

a) an esterification step that comprises:
a reaction section that is fed with a butanediol feedstock, with at least a fraction of the liquid pyrolysis effluent obtained from step c), and with the carboxylic acid effluent obtained from the separation section of step a), where said reaction section is implemented in the presence of an acid catalyst at a pressure of between 0.01 and 1.0 MPa and an MMH in the reaction section of between 0.05 and 25 $h^{-1}$, where MMH is equal to the molar flow rate of diol that feeds said section over the mole number of the catalyst in said section, a separation section that separates the effluent obtained from the reaction section into at least a diester effluent of butanediol, a water effluent, and a carboxylic acid effluent;

b) a pyrolysis step that comprises a pyrolysis reactor that is fed with at least a fraction of the diester effluent of butanediol obtained from esterification step a) and a fraction of the washing effluent obtained from step c), where said reactor is operated at a temperature of between 500 and 650° C. and said step produces a pyrolysis effluent, c) a step for separation of said pyrolysis effluent obtained from step b) such as to produce at least a liquid pyrolysis effluent, a butadiene effluent, and a washing effluent and that comprises at least:

a section for cooling said pyrolysis effluent to a temperature of less than 150° C. and for producing a liquid pyrolysis effluent and a steam pyrolysis effluent;

a gas-liquid washing section that is fed at the top with a fraction of the diester effluent of butanediol obtained from step a) and at the bottom with the steam pyrolysis effluent and that produces a butadiene effluent at the top and a washing effluent at the bottom.

A first advantage of the invention is the fact that, since the diester effluent of butanediol that is produced at the esterification step is dry (that is, contains little or no water), the steam pyrolysis effluent, a butadiene-rich gaseous effluent, is not brought into contact with water, thus making it possible to eliminate the drying steps.

A second advantage of the invention is the fact that the diester that is used as a washing solvent employed in the invention does not have to undergo a specific regeneration step. In point of fact, the latter can be sent directly to the pyrolysis step because it principally contains diester and a little bit of acetic acid, which does not alter the yield of the conversion of diester into butadiene.

Another advantage of the invention is that it produces a 1,3-butadiene of high purity with good yields without drastically increasing investment or operating costs. The unit purification operations that are carried out also generate effluents that can easily be recycled into other unit operations of the method, thereby limiting the production of waste generated by the method overall.

DETAILED DESCRIPTION OF THE INVENTION

Feedstock

According to the invention, the method is fed with a butanediol feedstock that comprises at least 90% by weight of butanediol. Butanediol is defined as a compound that is selected from among the isomers of butanediol and mixtures thereof. Preferably, the feedstock contains more than 90% by weight of 2,3-butanediol or more than 90% by weight of 1,4-butanediol. Said butanediol feedstock can also contain water.

Butanediol Esterification Step a)

The conversion method according to the invention comprises an esterification step a) that comprises a reaction section that is fed with a butanediol feedstock and with at least a fraction of the liquid pyrolysis effluent obtained from step c), and with the carboxylic acid effluent obtained from the separation section of step a) and optionally with a make-up of carboxylic acid and that produces the corresponding diester and water, also comprising at least one separation section that separates the effluent from the reaction section into at least one diester effluent of butanediol, a water effluent, and a carboxylic acid effluent. The liquid pyrolysis effluent obtained from step c) is rich in carboxylic acid.

Preferably, the carboxylic acid used is selected from among formic acid, acetic acid, propanoic acid, butanoic acid, or benzoic acid. In a very preferred way, the carboxylic acid used is acetic acid.

Said reaction section can be implemented in any way well known to one skilled in the art. Said section is implemented in the presence of an acid catalyst, which can be homogeneous or heterogeneous, as is known to one skilled in the art. The MMH in the reaction section (molar flow rate of diol that feeds said section over the catalyst mole number in said section) is between 0.05 and 25 $h^{-1}$ and preferably between 0.15 and 20 $h^{-1}$. Said section is operated at a pressure of between 0.01 and 1.0 MPa, preferably between 0.05 and 0.2 MPa, and very preferably between 0.08 and 0.12 MPa.

In a preferred manner, the reaction section of the esterification step is implemented in a reactive distillation column in which the butanediol feedstock is introduced into the top of the column and the carboxylic acid is introduced into the bottom of the column. The ratio of the molar flow rates of butanediol and carboxylic acid is between 2 and 6, preferably between 2 and 4, and very preferably between 2 and 3.5.

At the top, said reactive distillation column produces a distillate that is mainly composed of water that is produced by the esterification reaction and of carboxylic acid that is introduced in excess; and at the bottom, it produces a residue that is composed mainly of butanediol diester and optionally carboxylic acid. This conversion step is such that the conversion of butanediol into butanediol diester is greater than 95 mol %, and preferably greater than 99 mol %. Unfortunately, the catalysts used to catalyze the esterification reaction also catalyze secondary reactions that generate byproducts from the dehydration of the butanediol feedstock.

In the preferred arrangement where the esterification step comprises a reactive distillation column, if the acid catalyst is homogeneous, it is introduced into the top of the column with the butanediol feedstock; if the catalyst is heterogeneous, it is held in the reactive distillation column by means of a device that is well known to one skilled in the art.

The temperature of the column to be distilled is between the boiling point of the water produced at the top and that of the butanediol diester that is produced at the bottom. In the case where the carboxylic acid used is acetic acid, the temperature between the top and the bottom of the column to be distilled typically varies between 100 and 230° C.

Said esterification step a) comprises a separation section that treats the effluent from the reaction section, advantageously the distillate from said reactive distillation column, where the latter is mainly composed of water produced by the esterification reaction and carboxylic acid that is introduced in excess, but also byproducts that result from the dehydration of the butanediol feedstock. Said separation section makes it possible at least to produce a water effluent that is devoid of carboxylic acid and that is eliminated from the method; and a carboxylic acid effluent that is devoid of water, which is recycled to the reactive distillation column. This separation can be accomplished by any method that is well known to one skilled in the art. Preferably, in the case where acetic acid is used to carry out the esterification of the butanediol, this separation is accomplished by heterogeneous azeotropic distillation using a carrier. In a non-limiting fashion, this carrier can be isopropyl acetate, diethyl ether, or ethyl tert-butyl ether. Advantageously, the distillate from said reactive distillation column or the water effluent and the carboxylic acid effluent is (are) treated in such a way as to separate an effluent that contains the impurities produced by the secondary reactions.

Step b) for Pyrolysis of the Butanediol Diester

The conversion method according to the invention comprises a pyrolysis step that includes a pyrolysis reactor that is fed with at least a fraction of the butanediol diester effluent obtained from esterification step a), where said reactor is operated at a temperature of between 500 and 650° C. in such a way as to produce a pyrolysis effluent. The pyrolysis reaction can be implemented with or without the presence of a catalyst.

The pyrolysis reaction mainly transforms one mole of butanediol diester into one mole of 1,3-butadiene and thus releases two moles of carboxylic acid. "Mainly" is defined to mean that more than 70 mol % of the butanediol diester is converted into 1,3-butadiene. Preferably, more than 80 mol % of the butanediol diester is converted into 1,3-butadiene. Said pyrolysis reactor, also called a pyrolysis furnace, is operated at a temperature of between 500 and 650° C., preferentially between 550 and 600° C., and more preferably between 575 and 585° C. The optimum contact time within the pyrolysis furnace is a function of the partial pressure of the butanediol diester that is injected into the pyrolysis furnace. This time is typically 1 second for a partial pressure of butanediol diester of 0.1 MPa and 7 seconds for a partial pressure of butanediol diester of 0.04 MPa. The partial pressure is advantageously adjusted by adding an inert diluent such as nitrogen, carbon dioxide, methane, or acetic acid.

Separation Step c)

The separation step c) is fed with said pyrolysis effluent that is obtained from step b) and comprises at least:
  a section for cooling said pyrolysis effluent to a temperature of less than 150° C., producing a liquid pyrolysis effluent and a steam pyrolysis effluent;
  a gas-liquid washing section that is fed with a fraction of the butanediol diester effluent obtained from step a) at the top and with said steam pyrolysis effluent at the bottom.

The effluent obtained from said pyrolysis reactor is rapidly cooled to a temperature of less than 150° C., preferably less than 50° C., in such a way as to limit the formation of degradation products, for example by the Diels-Alder reaction of 1,3-butadiene on itself to form vinyl cyclohexene (VCH). This step is advantageously implemented by quenching (or "quench", to take the English term). "Quenching" is defined to mean bringing a fluid to be cooled, in this case the pyrolysis effluent, into close contact with a cold fluid. Quenching is carried out, for example, inside a quenching tower in which the effluent obtained from said pyrolysis reactor (i.e., a hot substance) is introduced at the bottom and is brought into counter-current contact with a (cold) quenching liquid that is sprayed at the top of said quenching tower. Thus, the quenching tower produces a liquid pyrolysis effluent that is drawn off at the bottom and a steam pyrolysis effluent that is drawn off at the top.

According to a particular arrangement of the invention, said quenching liquid is a fraction of said liquid pyrolysis effluent that is produced by said quenching tower and that is pre-cooled before being reintroduced into the quenching tower. Preferably, this fraction of said liquid pyrolysis effluent is cooled to below 50° C. and preferably to below 40° C.

In one embodiment of the invention, said liquid pyrolysis effluent is purified before being recycled to step a). This purification can be accomplished by any techniques known to one skilled in the art. It is possible to cite, in a non-limiting manner, distillation, pressure-change distillation, heterogeneous azeotropic distillation with the addition of a carrier, or else adsorption on a solid. The technique that is employed depends greatly on the butanediol feedstock used. As a matter of fact, the liquid byproducts produced at the pyrolysis step are greatly dependent on the butanediol diester isomer that is treated.

In another embodiment of the invention, said liquid pyrolysis effluent is returned to step a) without being purified, in view of its highly pure carboxylic acid.

In the embodiment where the liquid pyrolysis effluent is purified for the purpose of recycling it to step a), it is advantageous to use a fraction of the purified liquid pyrolysis effluent to feed the quenching tower. This implementation makes it possible to reduce the content of impurities within the quenching tower and thus to obtain a steam pyrolysis effluent of higher purity.

Said steam pyrolysis effluent comprises more than 80% by weight and preferably more than 90% by weight of 1,3-butadiene (without taking into account the optional inert diluent used to reduce the partial pressure of butanediol diester inside the pyrolysis furnace). Said steam pyrolysis effluent can also contain light organic compounds that are produced at the pyrolysis step or during the cooling of the effluent.

Said steam pyrolysis effluent feeds the bottom of a gas-liquid washing column, which is fed at the top with a fraction of the butanediol diester effluent obtained from step a). Said gas-liquid washing column produces at the top a butadiene effluent and at the bottom a washing effluent that can be recycled to pyrolysis step b).

Said gas-liquid washing column is operated at a pressure that is advantageously between 0.01 and 1 MPa and preferably between 0.05 and 0.5 MPa and advantageously comprises between 1 and 10 theoretical steps and preferably between 1 and 5 theoretical steps. The mass ratio of butanediol diester effluent to steam pyrolysis effluent is advantageously between 1 and 10 and advantageously between 1 and 5, and very advantageously between 2 and 4. The steam pyrolysis effluent is advantageously fed at a temperature of less than 150° C. and preferably less than 50° C. The butanediol diester effluent is advantageously fed at a temperature of less than 150° C. and preferably less than 50° C.

Advantageously, said steam pyrolysis effluent can be compressed and/or cooled before being introduced into said gas-liquid washing column in order to improve the efficiency of the gas-liquid washing.

Said liquid pyrolysis effluent is composed in the majority of carboxylic acid. "In the majority" is defined as at least 50% by weight and preferably at least 70% by weight. Said effluent can also comprise other organic compounds such as, for example, unconverted butanediol diester, intermediate products of pyrolysis (that is, molecules of butanediol diester that have lost one carboxylic acid fragment of the two that are required for the formation of 1,3-butadiene) and optional byproducts.

The butadiene effluent can undergo any later purification step known to one skilled in the art, depending on the required purity specifications, where these specifications are dictated by the later use envisioned.

Figure 1:
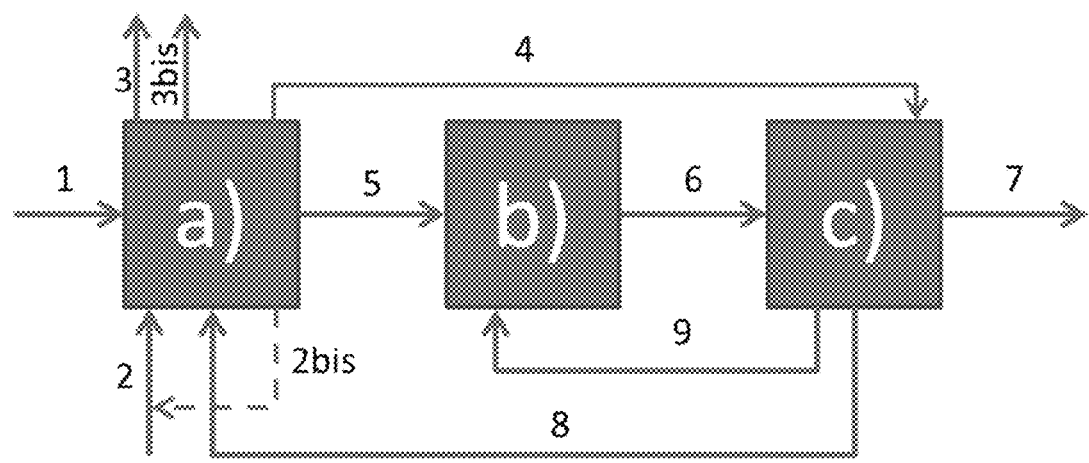
FIG. 1 depicts a schematic view of an arrangement of the method according to the invention.

Unit a), which corresponds to step a), comprises a reaction section and a separation section, not shown in the figure. The butanediol feedstock (1), a make-up of carboxylic acid (2), and the liquid pyrolysis effluent (8) feed the reaction section of esterification step a). The separation section produces a water effluent (3), an impurity effluent (3a), a butanediol diester effluent (4) and (5), and a carboxylic acid effluent (2a). The carboxylic acid effluent (2a) obtained from the separation section feeds the reaction section of step a).

One fraction of the butanediol diester effluent (5) feeds a pyrolysis step b) that produces a pyrolysis effluent (6) that feeds a separation step c).

The separation step c) is fed with the other fraction of the butanediol diester effluent (4) that is produced by step a) and with the pyrolysis effluent (6) obtained from step b). The separation step c) produces a liquid pyrolysis effluent (8) that is recycled to the esterification step a), a butadiene effluent (7), and a washing effluent (9) that is sent back to pyrolysis step b).

Figure 2:
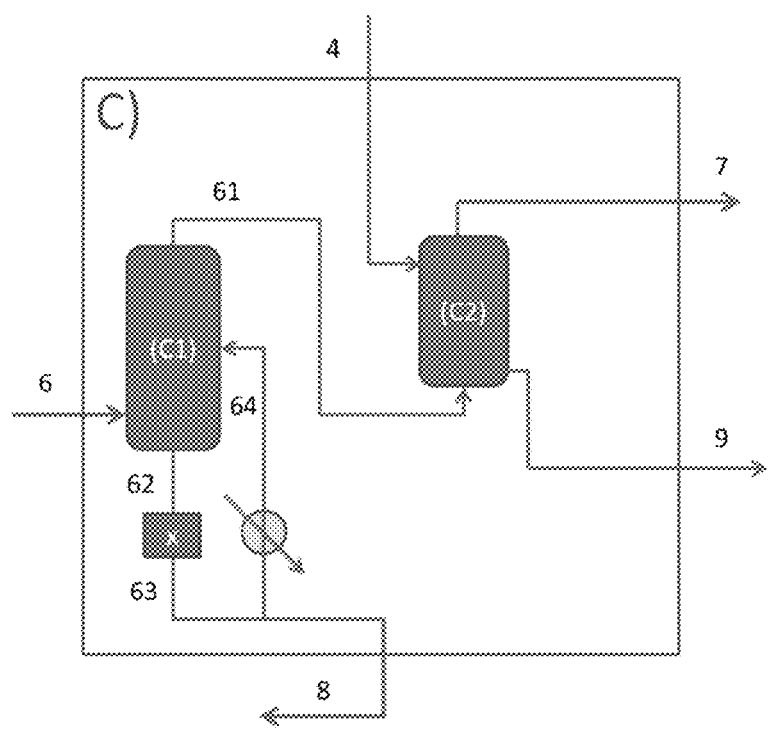

FIG. 2 depicts an arrangement of step c) according to the invention. The numeric references are identical for FIGS. 1 and 2.

A pyrolysis effluent (6) is introduced at the bottom of a quenching tower (C1). This quenching tower is fed at its top with a quenching liquid (64). This quenching tower produces, on the one hand, a steam pyrolysis effluent (61) that feeds a gas-liquid washing column (C2) and, on the other hand, a liquid pyrolysis effluent (62) that may optionally be purified in a purification section (X). One fraction of the liquid pyrolysis effluent (63) is cooled before being recycled (64) to the cooling tower (C1). The other fraction of the liquid pyrolysis effluent (8) is recycled to step a) of the method.

The steam pyrolysis effluent (61) is introduced at the bottom of the gas-liquid washing column (C2), which is fed at its top with a fraction of the butanediol diester effluent (4) that is produced at step a) of the method. Said gas-liquid washing column (C2) produces at its top a butadiene effluent (7) and at its bottom a washing effluent (9) that is sent back to pyrolysis step b).

EXAMPLE

A 2,3-butanediol feedstock is esterified in the presence of acetic acid. The effluent from the esterification step is separated into a butanediol diester effluent and an acetic acid effluent. A fraction of the diester effluent of 2,3-butanediol is pyrolyzed in a pyrolysis reactor, producing a pyrolysis effluent. The pyrolysis effluent is cooled to a temperature of 75° C. and is separated into a liquid pyrolysis effluent and a steam pyrolysis effluent.

The steam pyrolysis effluent feeds a gas-liquid washing column at its bottom at a temperature of 75° C.

In Example 1 (for comparison), this column is fed at the top with the acetic acid effluent at a temperature of 45° C.

In Example 2 (according to the invention), this column is fed at its top with the diester acid effluent of 2,3-butanediol at a temperature of 45° C.

The gas-liquid washing column is operated at a pressure of 0.1 MPa and comprises three theoretical steps. The ratio of the mass flow rate of solvent (acetic acid effluent, or 2,3-butanediol diester effluent) relative to the mass flow rate of gas is 3.

The molar fraction compositions of the flows are presented in the following table:

|  | Example 1 | | | | Example 2 | | |
| --- | --- | --- | --- | --- | --- | --- | --- |
| Molar Fraction | Steam Pyrolysis Effluent | Acetic Acid Effluent | Washing Effluent | butadiene Effluent | 2,3-butanediol Diester Effluent | Washing Effluent | Butadiene Effluent |
| 1,3-butadiene | 85.2% | 0.0% | 1.5% | 83.2% | 0.0% | 6.0% | 93.4% |
| Acetic Acid | 5.7% | 96.6% | 94.8% | 8.6% | 0.1% | 4.2% | 1.5% |
| Incondensibles (CO, $CH_4$, $CO_2$, $H_2$) | 5.2% | 0.0% | 0.1% | 5.1% | 0.0% | 3.4% | 1.8% |
| Intermediate Pyrolysis Products | 0.2% | 0.0% | 0.1% | 0.0% | 0.6% | 0.7% | 0.0% |
| $C_4$ Hydrocarbons | 1.9% | 0.0% | 0.1% | 1.6% | 0.0% | 0.1% | 2.1% |
| $C_{4+}$ Hydrocarbons | 1.5% | 0.0% | 0.4% | 0.5% | 0.0% | 0.9% | 0.6% |
| Polar Impurities (MEK, acetaldehyde) | 0.1% | 0.0% | 0.0% | 0.0% | 0.5% | 0.5% | 0.1% |
| Water | 0.3% | 3.3% | 3.0% | 0.9% | 0.0% | 0.2% | 0.1% |
| Acetic Anhydride | 0.0% | 0.0% | 0.0% | 0.0% | 0.0% | 0.0% | 0.0% |
| 2,3-butanediol Diacetate | 0.0% | 0.1% | 0.1% | 0.0% | 98.8% | 84.0% | 0.5% |

As is evident here, the washing of the steam pyrolysis effluent with the 2,3-butanediol diester effluent makes it possible to obtain a gas that is richer in 1,3-butadiene (93.4 mol %) compared to washing with the acetic acid effluent (83.2 mol %). This is due in particular to the fact that acetic acid is a relatively volatile compound that is thus found in large amounts in the purified gas (8.6 mol %) when acetic acid is used as a washing solvent.

In order to avoid losing this acetic acid, the washing effluent in accordance with Example 1 thus has then to be washed with water, adding a unit operation. Moreover, the acetic acid that is thus recovered has to be separated from the water. This is accomplished by heterogeneous azeotropic distillation and is thus relatively expensive.

By using the 2,3-butanediol diester effluent in accordance with the invention, a butadiene effluent is thus obtained that is of higher purity and that is produced at lower cost.

In addition, compared to Example 1, it is evident that the amount of 1,3-butadiene solubilized in the washing effluent is approximately 5 times greater in Example 2, as presented.

According to the invention, the washing effluent is sent back to the pyrolysis step. Thus, the 1,3-butadiene that is solubilized in the washing effluent is not lost: it turns around between the pyrolysis step and the gas-liquid washing column.

By contrast, in the case of Example 1, where the acetic acid effluent is used to wash the steam pyrolysis effluent, the washing effluent containing the acetic acid is sent back to the esterification step. This requires a recovery device that is adapted for solubilized 1,3-butadiene because, when the esterification step is carried out in reactive distillation, which is usually the case, the latter comes out in the distillate with the water and the acetic acid and thus goes on to heterogeneous azeotropic distillation, which is designed to separate the water from the acetic acid. The method according to the invention renders such an additional operation unnecessary and thus greatly streamlines the conventional system.

The invention claimed is:

1. Method for converting butanediol into butadiene that is fed with a butanediol feedstock, where said method comprises at least:

a) an esterification step that comprises:
   a reaction section that is fed with a butanediol feedstock, with at least a fraction of the liquid pyrolysis effluent obtained from step c), and with the carboxylic acid effluent obtained from the separation section of step a), where said reaction section is implemented in the presence of an acidic catalyst at a pressure of between 0.01 and 1.0 MPa and an MMH in the reaction section of between 0.05 and 25 $h^{-1}$, where MMH is equal to the molar flow rate of diol that feeds said section over the mole number of the catalyst in said section, and
   a separation section that separates the effluent obtained from the reaction section into at least a diester effluent of butanediol, a water effluent, and a carboxylic acid effluent;

b) a pyrolysis step that comprises a pyrolysis reactor that is fed, at least, with a fraction of the diester effluent of butanediol obtained from esterification step a) and with a fraction of the washing effluent obtained from step c), where said reactor is operated at a temperature of between 500 and 650° C. and said step produces a pyrolysis effluent, and c) a step for separation of said pyrolysis effluent obtained from step b) comprising, at least:
   a section for cooling said pyrolysis effluent obtained from step b) to a temperature of less than 150° C. and for producing a cooled liquid pyrolysis effluent and a steam pyrolysis effluent; and
   a gas-liquid washing section that is fed at the top with a fraction of the diester effluent of butanediol obtained from step a) and at the bottom with the steam pyrolysis effluent and that produces a butadiene effluent at the top and a washing effluent at the bottom.

2. Method in accordance with claim 1 in which said reaction section of said step a) is also fed with a make-up of carboxylic acid.

3. Method in accordance with claim 1 in which said reaction section of said step a) is implemented in a reactive distillation column in which the butanediol feedstock is introduced into the top part of the column and the carboxylic acid is introduced into the bottom part of the column, with the ratio of the molar flow rates of butanediol and carboxylic acid being between 2 and 6.

4. Method in accordance with claim 1 in which the carboxylic acid used is formic acid, acetic acid, propanoic acid, butanoic acid, or benzoic acid.

5. Method in accordance with claim 1 in which the carboxylic acid used is acetic acid.

6. Method in accordance with claim 5 in which said separation section of said step a) is implemented by heterogeneous azeotropic distillation using a carrier.

7. Method according to claim 1 in which the partial pressure of butanediol diester in pyrolysis step b) is adjusted by adding an inert diluent.

8. Method in accordance with claim 1 in which the pyrolysis effluent obtained from step b) is cooled to a temperature of less than 50° C. in the cooling section of step c).

9. Method in accordance with claim 1 in which the cooling section of step c) is implemented by quenching.

10. Method in accordance with claim 9 in which said quenching is carried out inside a quenching tower in which the effluent obtained from said pyrolysis reactor is introduced at the bottom and is brought into counter-current contact with a quenching liquid that is sprayed at the top of said quenching tower.

11. Method in accordance with claim 10 in which said quenching liquid is a fraction of said cooled liquid pyrolysis effluent produced by said quenching tower that is pre-cooled before being reintroduced into the quenching tower.

12. Method in accordance with claim 11 in which said fraction of said cooled liquid pyrolysis effluent is cooled to below 40° C.

13. Method in accordance with claim 1 in which said cooled liquid pyrolysis effluent is sent back to esterification step a) without intermediate purification.

14. Method in accordance with claim 1 in which said cooled liquid pyrolysis effluent is purified before being recycled to esterification step a).

15. Method in accordance with claim 1 in which said steam pyrolysis effluent is compressed and/or cooled before being introduced into said gas-liquid washing section.

16. Method according to claim 7 wherein the inert is nitrogen, carbon dioxide, methane or acetic acid.

* * * * *